US009606028B2

(12) United States Patent
Detweiller et al.

(10) Patent No.: US 9,606,028 B2
(45) Date of Patent: Mar. 28, 2017

(54) AERIAL WATER SAMPLER

(71) Applicant: NUtech Ventures, Lincoln, NE (US)

(72) Inventors: Carrick Detweiller, Lincoln, NE (US);
John-Paul Ore, Seward, NE (US);
Baoliang Zhao, Lincoln, NE (US);
Sebastian Elbaum, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 105 days.

(21) Appl. No.: 14/621,733

(22) Filed: Feb. 13, 2015

(65) Prior Publication Data
US 2015/0268136 A1    Sep. 24, 2015

Related U.S. Application Data

(60) Provisional application No. 61/939,786, filed on Feb. 14, 2014.

(51) Int. Cl.
*B64C 29/00* (2006.01)
*G01N 1/10* (2006.01)
(Continued)

(52) U.S. Cl.
CPC .............. *G01N 1/14* (2013.01); *B64C 39/024* (2013.01); *G01S 15/025* (2013.01); *G01S 15/08* (2013.01);
(Continued)

(58) Field of Classification Search
CPC ... B64D 1/00; B64C 39/024; B64C 2201/108; B64C 2201/162; G01N 1/2273;
(Continued)

(56) References Cited

U.S. PATENT DOCUMENTS 2,488,486 A * 11/1949 Worzel .................. E21B 25/18
175/403
2,717,656 A * 9/1955 Bannister ............... G01V 1/047
102/311
(Continued)

FOREIGN PATENT DOCUMENTS

| CN | 203975222 U | * | 12/2014 |
| CN | 105571904 A | * | 5/2016 |
| EP | 2584355 | | 4/2013 |

OTHER PUBLICATIONS

Bernard et al., "Generic Slung Load Transportation System Using Small Size Helicopters", 2009 IEEE International Conference on Robotics and Automation, May 12-17, 2009.*
(Continued)

*Primary Examiner* — David A Rogers
(74) *Attorney, Agent, or Firm* — Fish & Richardson P.C.

(57) ABSTRACT

In one aspect, a vehicle includes an aerial propulsion system, an altitude sensor system, a water sampling system, and a control system. The water sampling system includes a water sampling extension configured to extend away from the vehicle, one or more water sample receptacles, and a water pump. The control system is configured to perform operations including: guiding, using the aerial propulsion system, the vehicle over a water source; causing, using sensor data from the altitude sensor system, the vehicle to descend towards the water source so that the water sampling extension contacts the water source; and causing, using the water sampling system, the water pump to pump water from the water source into the one or more water sample receptacles through the water sampling extension while the vehicle is in flight over the water source.

20 Claims, 7 Drawing Sheets

(51) Int. Cl.
| | |
|---|---|
| G01N 1/14 | (2006.01) |
| G01S 15/08 | (2006.01) |
| G05D 1/04 | (2006.01) |
| B64C 39/02 | (2006.01) |
| G01S 15/02 | (2006.01) |
| G05D 1/10 | (2006.01) |
| G01N 1/02 | (2006.01) |

(52) U.S. Cl.
CPC .............. *G05D 1/042* (2013.01); *G05D 1/102* (2013.01); *B64C 2201/024* (2013.01); *B64C 2201/12* (2013.01); *B64C 2201/141* (2013.01); *G01N 1/10* (2013.01); *G01N 2001/021* (2013.01)

(58) Field of Classification Search
CPC .... G01N 1/24; G01N 2001/2285; G01N 1/12; G01N 1/10; G01N 1/14; G01N 2001/1031; G01N 2001/2279; G01C 5/005; G05D 1/042
See application file for complete search history.

(56) References Cited

U.S. PATENT DOCUMENTS

| | | | | |
|---|---|---|---|---|
| 2,914,950 | A * | 12/1959 | Giguere | A01K 97/00 175/238 |
| 3,327,968 | A * | 6/1967 | Converse | B64D 1/22 114/244 |
| 3,462,995 | A | 8/1969 | Weiss | |
| 3,977,479 | A * | 8/1976 | Sainsbury | E21B 1/02 173/185 |
| 4,659,675 | A * | 4/1987 | Demaison | G01V 9/007 436/141 |
| 4,744,256 | A | 5/1988 | Niskin | |
| 5,722,618 | A * | 3/1998 | Jacobs | B64D 9/00 244/137.1 |
| 6,705,573 | B2 * | 3/2004 | McDonnell | B64D 3/02 102/336 |
| 6,796,194 | B1 * | 9/2004 | Ryan | G01N 1/20 73/290 R |
| 6,840,121 | B2 * | 1/2005 | Thomas | G01N 1/14 73/863.31 |
| 6,854,344 | B2 * | 2/2005 | Cornish | G01N 1/2252 73/863.22 |
| 7,716,980 | B1 * | 5/2010 | Colten | G01P 5/165 73/170.02 |
| 7,998,731 | B2 * | 8/2011 | Daitch | G01N 1/2273 435/287.4 |
| 8,599,646 | B2 * | 12/2013 | Pochon | G01S 7/023 367/99 |
| 8,820,672 | B2 | 9/2014 | Erben et al. | |
| 8,855,838 | B2 * | 10/2014 | Berthier | B64C 31/036 701/1 |
| 8,989,924 | B2 * | 3/2015 | Seydoux | A63H 27/12 244/17.13 |
| 2004/0118222 | A1 * | 6/2004 | Cornish | G01N 1/2252 73/863.22 |
| 2004/0185554 | A1 * | 9/2004 | Daitch | G01N 1/2273 435/309.1 |
| 2008/0027647 | A1 * | 1/2008 | Ansell | G01S 13/723 701/301 |
| 2010/0152933 | A1 | 6/2010 | Smoot et al. | |
| 2014/0047932 | A1 * | 2/2014 | Coote | G01N 1/08 73/863.23 |
| 2014/0212986 | A1 * | 7/2014 | Angelescu | G01N 1/12 436/180 |

OTHER PUBLICATIONS

Schwarzbach et al., "Helicopter UAV Systems for in situ Measurements and Sensor Placement", 2012 IEEE International Geoscience and Remote Sensing Symposium, Jul. 2012.*

Ryan Roberston, "Drones to Fly in Nebraska Skies", On the Internet at <http://netnebraska.org/article/news/drones-fly-nebraska-skies>, Jan. 10, 2013.*

Anderson et al, "Lightweight unmanned aerial vehicles will revolutionize spatial ecology," Frontiers in Ecology and the Environment, 2013, 11.3: 138-146.

Aquacopters (2012). Aquacopters. http://www.aquacopters.com/. [Online; accessed Jun. 15, 2014].

"Ascending Technologies." [Online]. Available: http://www.asctec.de.

Bird et al, "Development of an active, large volume, discrete seawater sampler for autonomous underwater vehicles," OCEANS 2007. IEEE, 2007.

Clothier et al, "The safety risk management of unmanned aircraft systems," Handbook of Unmanned Aerial Vehicles. Springer Netherlands, 2014. 2229-2275.

Cruz et al, "The MARES AUV, a modular autonomous robot for environment sampling," OCEANS 2008. IEEE, 2008.

Dunbabin et al, "Experimental evaluation of an autonomous surface vehicle for water quality and greenhouse gas emission monitoring," Robotics and Automation (ICRA), 2010 IEEE International Conference on. IEEE, 2010.

Dunbabin et al, "An autonomous surface vehicle for water quality monitoring," Australasian Conference on Robotics and Automation (ACRA). 2009.

Faust et al, "Learning swing-free trajectories for uays with a suspended load," Robotics and Automation (ICRA), 2013 IEEE International Conference on. IEEE, 2013.

Harel, "Statecharts: A visual formalism for complex systems," Science of computer programming 8.3 (1987): 231-274.

Itopf, I. (2012). Sampling and Monitoring of Marine Oil Spills. http://www.itopf.com/information-services/publications/documents/TIP14SamplingandMonitoringofMarineOilSpills.pdf. [Online; accessed Jul. 1, 2014].

Jain et al, "Autonomous river exploration," Field and Service Robotics. Springer International Publishing, 2015.

Kendoul et al, "Survey of advances in guidance, navigation, and control of unmanned rotorcraft systems," Journal of Field Robotics 29.2 (2012): 315-378.

Maxbotix (2014). MaxBotix Ultrasonic Sensors. http://www.maxbotix.com. [Online; accessed Jun. 15, 2014].

Merz et al, "Dependable Low-altitude Obstacle Avoidance for Robotic Helicopters Operating in Rural Areas," Journal of Field Robotics, 2013, 30.3: 439-471.

Merz et al, "Control system framework for autonomous robots based on extended state machines," Autonomic and Autonomous Systems, 2006. ICAS'06. 2006 International Conference on. IEEE, 2006.

Michael et al, "Cooperative manipulation and transportation with aerial robots," Autonomous Robots, 2011, 30.1: 73-86.

Neumann et al, "Autonomous gas-sensitive microdrone: Wind vector estimation and gas distribution mapping," Robotics & Automation Magazine, IEEE, 2012, 19.1: 50-61.

Ore et al, "Autonomous aerial water sampling," Journal of Field Robotics, 2015.

QuadH2O (2014). Water Resistant Multirotor. http://www.quadh2o.com/. [Online; accessed Jun. 30, 2014].

Rahimi et al, "Adaptive sampling for environmental robotics," Robotics and Automation, 2004. Proceedings. ICRA'04. 2004 IEEE International Conference on. vol. 4. IEEE, 2004.

Ritz et al, "Carrying a flexible payload with multiple flying vehicles," Intelligent Robots and Systems (IROS), 2013 IEEE/RSJ International Conference on. IEEE, 2013.

"Robot Operating System." [Online] Available: http://www.ros.org.

Ross et al, "Learning monocular reactive uav control in cluttered natural environments," Robotics and Automation (ICRA), 2013 IEEE International Conference on. IEEE, 2013.

Scherer et al, "Flying fast and low among obstacles," Robotics and Automation, 2007 IEEE International Conference on. IEEE, 2007.

Schwarzbach et al, "Remote water sampling using flying robots," Unmanned Aircraft Systems (ICUAS), 2014 International Conference on. IEEE, 2014.

(56) References Cited

OTHER PUBLICATIONS

Sreenath et al, "Trajectory generation and control of a quadrotor with a cable-suspended load-A differentially-flat hybrid system," Robotics and Automation (ICRA), 2013 IEEE International Conference on. IEEE, 2013.
TCSMicropumps (2014). TCS Micropumps, UK. Model M200S-SUB. http://micropumps.co.uk/TCSM200range.htm. [Online; accessed Jun. 15, 2014].
Thomas et al, "Feb. 7, 2013, Avian-Inspired Grasping for Quadrotor Micro UAVs," 2013.
"VICON." [Online] Available: http://www.vicon.com.
Wurm et al, "OctoMap: A probabilistic, flexible, and compact 3D map representation for robotic systems," Proc. of the ICRA 2010 workshop on best practice in 3D perception and modeling for mobile manipulation. vol. 2. 2010.
Zhang et al, "Adaptive sampling for estimating a scalar field using a robotic boat and a sensor network," Robotics and Automation, 2007 IEEE International Conference on. IEEE, 2007.

\* cited by examiner

AERIAL WATER SAMPLER

CROSS-REFERENCE TO RELATED APPLICATIONS

This application claims the benefit under 35 U.S.C. §119 (e) of U.S. Patent Application No. 61/939,786, entitled "Aerial Water Sampler," filed Feb. 14, 2014, which is incorporated herein by reference in its entirety.

STATEMENT AS TO FEDERALLY SPONSORED RESEARCH

This invention was made with government support under grants from NSF (NSF IIS-1116221, NSF CSR-1217400), USDA-NIFA (#2013-67021-20947), and AFSOR (AFOSR #FA9550-10-1-0406). The government has certain rights in the invention.

TECHNICAL FIELD

This disclosure relates generally to obtaining water samples using an aerial vehicle.

BACKGROUND

Clean water is essential to our livelihoods, yet controlling water quality is an ongoing challenge. Characterizing water sources can be challenging due to insufficient data, e.g., a lack of data on water quality variations due to the spatial distribution of water transport pathways and contaminant source areas. This lack of data can inhibit the understanding of transport processes and the development of effective management plans to address water quality issues. Some water sampling techniques are based on grab sampling (e.g. dipping a bottle off the side of a kayak), statically deployed collection systems, or using mobile sensors affixed to Autonomous Surface Vehicles (ASVs) or Autonomous Underwater Vehicles (AUVs). Some autonomous systems are used on large, open water features such as seas, large lakes and rivers, and sample for long duration, in deep or distant places, with high quality.

SUMMARY

In general, one innovative aspect of the subject matter described in this specification can be implemented in an aerial water sampler. In one aspect, a vehicle includes an aerial propulsion system, an altitude sensor system, a water sampling system, and a control system. The water sampling system includes a water sampling extension configured to extend away from the vehicle, one or more water sample receptacles, and a water pump. The control system is configured to perform operations including: guiding, using the aerial propulsion system, the vehicle over a water source; causing, using sensor data from the altitude sensor system, the vehicle to descend towards the water source so that the water sampling extension contacts the water source; and causing, using the water sampling system, the water pump to pump water from the water source into the one or more water sample receptacles through the water sampling extension while the vehicle is in flight over the water source.

These and other implementations can each optionally include one or more of the following features. The altitude sensor system includes: a plurality of ultrasonic rangers configured to face the water source; and an air pressure sensor. Guiding the vehicle includes determining that the altitude of the vehicle is greater than a threshold altitude and, in response, using the air pressure sensor to estimate the altitude of the vehicle and guide the vehicle. Causing the vehicle to descend towards the water source includes estimating the altitude of the vehicle using a Kalman filter and a plurality of ultrasonic readings from the ultrasonic rangers and a plurality of pressure readings from the air pressure sensor. The altitude sensor system includes a plurality of ultrasonic rangers configured to face the water source, and causing the vehicle to descend towards the water source includes applying a scoring heuristic to a plurality of ultrasonic readings from the ultrasonic rangers. Applying the scoring heuristic includes discarding ultrasonic readings outside of a programmed maximum range of the ultrasonic sensors. Applying the scoring heuristic includes scoring the ultrasonic readings based on a respective proximity, for each ultrasonic reading, to a current altitude estimate maintained by the control system. The vehicle is an unmanned rotorcraft including a plurality of rotors. The control system is configured to autonomously guide the vehicle to a plurality of water sampling sites and cause the water sampling system to store a water sample from each of the water sampling sites into a respective water sample receptacle. The operations include, after guiding the vehicle to a second water sampling site, flushing water from the water sampling system from a first water sampling site using water from the second water sampling site.

The details of one or more disclosed implementations are set forth in the accompanying drawings and the description below. Other features, aspects, and advantages will become apparent from the description, the drawings and the claims.

DETAILED DESCRIPTION

Figure 1:
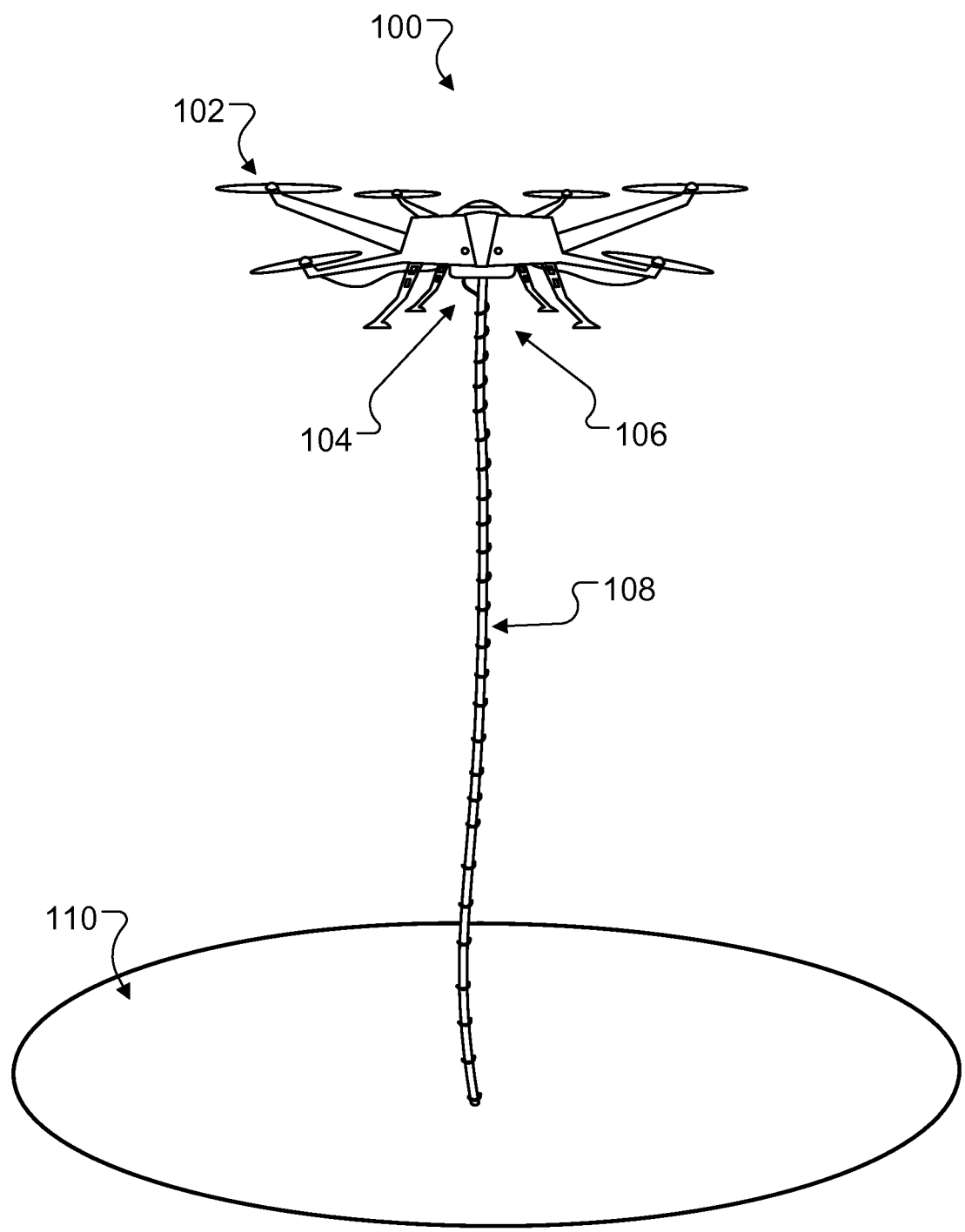
FIG. 1 is a diagram illustrating an example aerial water sampler.

FIG. 1 is a diagram illustrating an example aerial water sampler 100. The aerial water sampler 100 can be an unmanned aerial vehicle (UAV), e.g., a rotorcraft including multiple rotors, that is configured to collect water samples. The aerial water sampler 100 includes an aerial propulsion system 102, an altitude sensor system 104, and a water sampling system 106 that includes a water sampling extension 108 configured to extend into a water source 110 and a pump 112. The pump 112 can be at the end of the water sampling extension 108, as illustrated, or at any appropriate location on the aerial water sampler 100.

In operation, the aerial water sampler 100 uses the aerial propulsion system 102 to move the sampler 100 over the water source 110 and then descend towards the water source so that the water sampling extension 108 contacts and then submerges into the water source 110. While descending, the aerial water sampler 100 uses the altitude sensor system 104 to estimate the altitude of the aerial water sampler 100. Then, while the aerial water sampler 100 is in flight over the water source 110, the water sampling system 106 pumps water from the water source 110 into a water sample receptacle through the water sampling extension 108.

The altitude sensor system 104 can include ultrasonic rangefinders that face the water source 110 and an air pressure sensor. Any appropriate type of rangefinder can be used in place of or in addition to the ultrasonic rangefinders. The aerial water sampler 100 can use the ultrasonic rangefinders or the air pressure sensor or both to determine an altitude for the aerial water sampler 100, e.g., depending on a current estimate of the aerial water sampler's altitude. The aerial water sampler 100 can also include other optional sensor systems, e.g., a digital camera that for supplying a video feed to a remote human operator. Estimating an altitude is described further below with reference to FIG. 5.

The water sampling system 106 includes one or more water sample receptacles, the pump 112, and the water sampling extension 108. The water sampling extension 108 can be a flexible tube that hangs from the aerial water sampler 100. In some examples, the tube is about 1.05 m long, which can strike a balance between the length of the tube and the flow rate of some pumps (7.5 ml/s at 1.05 m) when operated under normal operating conditions of the pumps. The tube material can be selected so that the tube is flexible enough to curl under the aerial water sampler 100 during landing and rigid enough to dampen motion-induced oscillations.

In some examples, the tube is mounted below the center of mass of the unloaded vehicle, which can reduce changes in flight dynamics while pumping. In some examples, the water sampling extension 108 includes one or more retractable tubes. In some examples, the water sampling system 106 includes one or more filters, e.g., to discard the water and keep anything caught in the filter for analysis.

The water sample receptacles can be glass or plastic vials or other types of containers made from any appropriate material. The pump 112 can be any appropriate type of pump that meets size, weight, and power specifications for the aerial sampler 100. In some examples, the pump is enclosed in a sewn mesh filter to form a bag around the pump, which can be useful when pumping in shallow water where the pump 112 may hit the bottom. The mesh can be, e.g., a 1 mm-grained mesh, which protects the pump while allowing sufficient water flow. An example mechanism for the water sampling system is described further below with reference to FIG. 4.

Example aerial water samplers can be implemented, using the subject matter described in this specification, so as to realize one or more of the following advantages. An aerial water sampler can increase the ease, temporal resolution, and spatial scale of water sampling. An aerial water sampler can be easily transported by a human operator in a car or backpack to a study site. Since an aerial water sampler can remain in flight while sampling, the aerial water sampler does not need to be waterproofed or completely waterproofed, which can reduce the weight and power specifications of the sampler and improve the efficiency of swapping water sample receptacles or batteries or other components. Remaining in flight while sampling can also be useful because the sampler can avoid contamination by the water, e.g., if the sampler is used to sample water for invasive species or radioactivity.

Furthermore, an aerial water sampler can be implemented using commercially available components, e.g., by adapting a commercially available micro-UAV. An aerial water sampler can travel nearly a kilometer and back, and will be able to travel further as battery technology and other propulsion technology continues to improve. An aerial water sampler can collect one or multiple water samples, e.g., three 20 ml water samples per flight. An altitude estimation system can enable reliable, low-altitude flight over water. An aerial water sampler can be used in a variety of settings, e.g., to characterize fresh water, to characterize sea water after an oil spill, or to transport water for other purposes, e.g., fire suppression.

Figure 2:
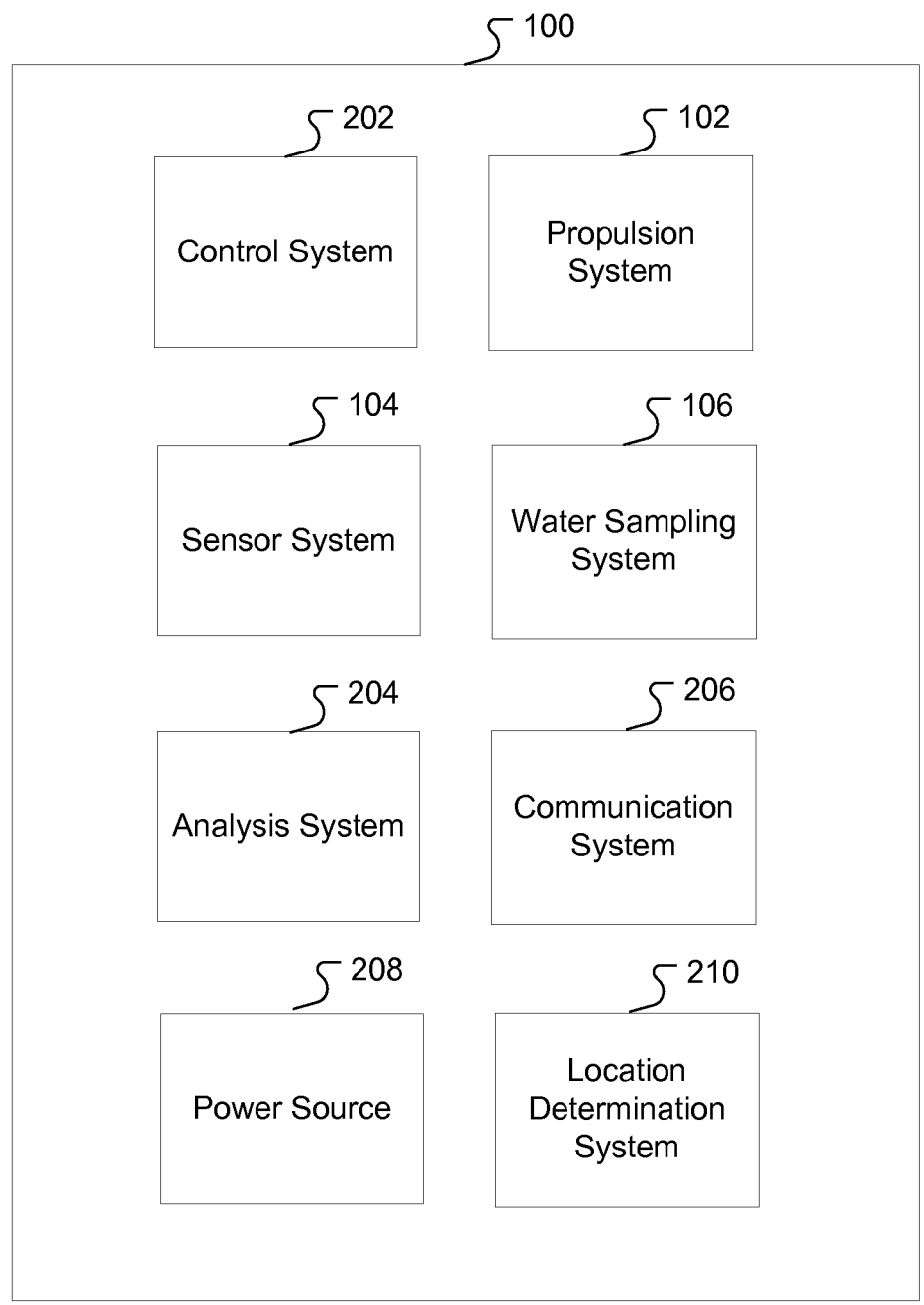
FIG. 2 is a block diagram illustrating component systems of the aerial water sampler.

FIG. 2 is a block diagram illustrating component systems of the aerial water sampler 100. The aerial water sampler 100 includes the aerial propulsion system 102, altitude sensors system 104, and water sampling system 106 illustrated in FIG. 1, and the aerial water sampler 100 can also include a control system 202, an analysis system 204, and a communication system 206. The aerial water sampler can also include a power source 208, e.g., a battery, and a location determination system 210, e.g., a Global Positioning System (GPS) system.

The control system 202 includes one or more processors and one or more computer readable storage devices storing code for controlling the aerial water sampler 100. For example, the control system 202 can be an embedded controller or other type of microcontroller that is configured, by virtue of the code stored on the control system, to control one or more of the component systems of the aerial water sampler 100. The control system 202 can be configured to control the aerial propulsion system 102 to cause the aerial water sampler 100 to hover in place, to ascend and descend, and to navigate to a specified location using the location determination system 210.

The analysis system 204, which is optional, is configured to analyze a water sample obtained by the water sampling system 106. For example, the aerial water sampler 100 can obtain a water sample and, using the analysis system 204, perform an onboard, onsite analysis of the sample and then determine, e.g., using the control system 202, to take one or more actions based on a result provided by the analysis system 204. The actions can include, e.g., keeping the obtained sample and proceeding to another site, flushing the obtained sample and obtaining another water sample, flushing the sample and proceeding to another site, or flushing the sample and returning to a base station. In some examples, the analysis system 204 is configured for pumping water through one or more filters to collect biological or other materials on the filters.

The communication system 206 can be any appropriate system for communication with the aerial water sampler 100. For example, the communication system 206 can include one or more radios configured to communicate digital data between the control system 202 and a base station computing system. In some examples, the communication system 206 includes two 2.4 GHz 802.15.4 radios for remote autonomous control and sensor feedback. In some examples, the aerial water sampler 100 is configured to be fully autonomous, e.g., by virtue of being programmed prior to a mission, so that no communication system is required.

Figure 3:
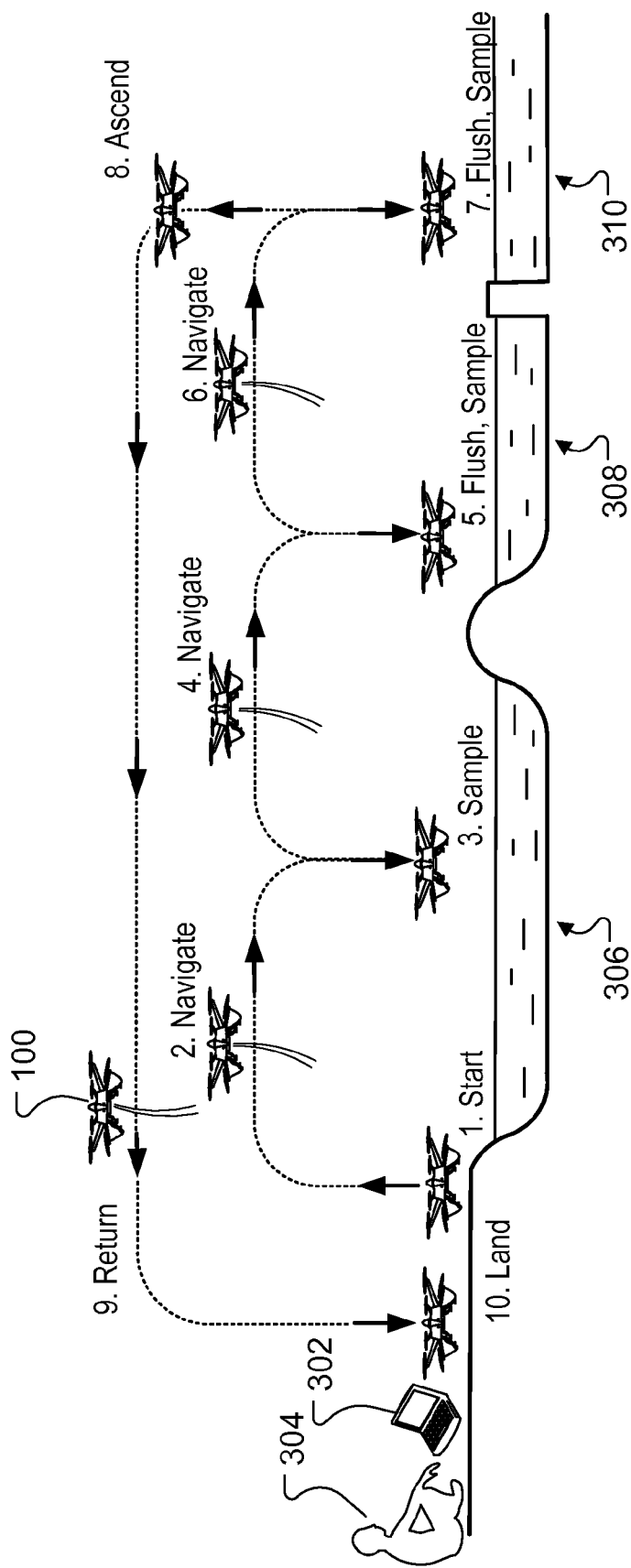
FIG. 3 is a diagram illustrating the aerial water sampler completing a water sampling mission.

FIG. 3 is a diagram illustrating the aerial water sampler 100 completing a water sampling mission. On the mission, the aerial water sampler 100 is configured by a human operator 304 using a base station computing system 302. For example, the base station computing system 302 can communicate with the control system 202 of the aerial water sampler 100 using the communication system 206 so that the base station computing system 302 can provide location coordinates of water sampling sites.

The aerial water sampler 100 starts at a base station and navigates to a first water sampling site 306. The aerial water sampler 100 can surmount obstacles such as dams, bridges, or land. While flying, the aerial water sampler 100 can monitor internal and external factors to determine a current risk level to avoid accidents. At the first water sampling site 306, the aerial water sampler 100 descends over the water and, while in flight over the water, obtains a first water sample.

The aerial water sampler 100 then navigates to a second water sampling site 308 and flushes the water sampling system by drawing water from the second water sampling site 308 through the water sampling system to clear out residual water from the first water sampling site 306. The duration of the flushing phase and the other sampling phases can be configurable, e.g., by the base station computing system 302 programming the duration into the control system 202. In some examples, the duration defaults to 20 s, which can be three times the duration used to fill a 20 ml vial. After flushing, the aerial water sampler 100 obtains a second water sample from the second water sampling site 308.

The aerial water sampler 100 navigates to a third water sampling site 310 and flushes the water sampling system by drawing water from the third water sampling site 310 to clear out residual water from the second water sampling site 308. Then, the aerial water sampler 100 obtains a third water sample from the third water sampling site 310. The aerial water sampler 100 ascends and returns to the base station.

The aerial water sampler 100 can submerge the water sampling extension 108 to a configurable depth, e.g., to sample at the surface or below the surface. The depth can be configured by appropriate programming of the control system 202. The aerial water sampler 100 can estimate the depth of the water sampling extension 108 in the water using the altitude sensor system 104 or water conductivity sensors spaced apart on the water sampling extension 108 or both. In some examples, the aerial water sampler 100 obtains more than one sample at a sampling site. For example, the aerial water sampler 100 can obtain a first sample near the surface of the water and a second sample deeper in the water than the first sample. The aerial water sampler 100 can flush the water sampling system between the first and second samples.

After the mission, the human operator 304 collects the water samples from the aerial water sampler and, if further samples are desired, the human operator 304 can start another mission. The water samples can be taken to a laboratory for analysis, e.g., to determine chemical properties such as phosphate, total phosphorous, nitratenitrite, nitrogen, and ammonia, as well as biological properties, such as the presence of toxic microcystins. At the base station, the human operator can monitor the aerial water sampler 100 during the mission and remotely control the aerial water sampler 100 as a backup pilot using the base station computing system 302.

Figure 4:
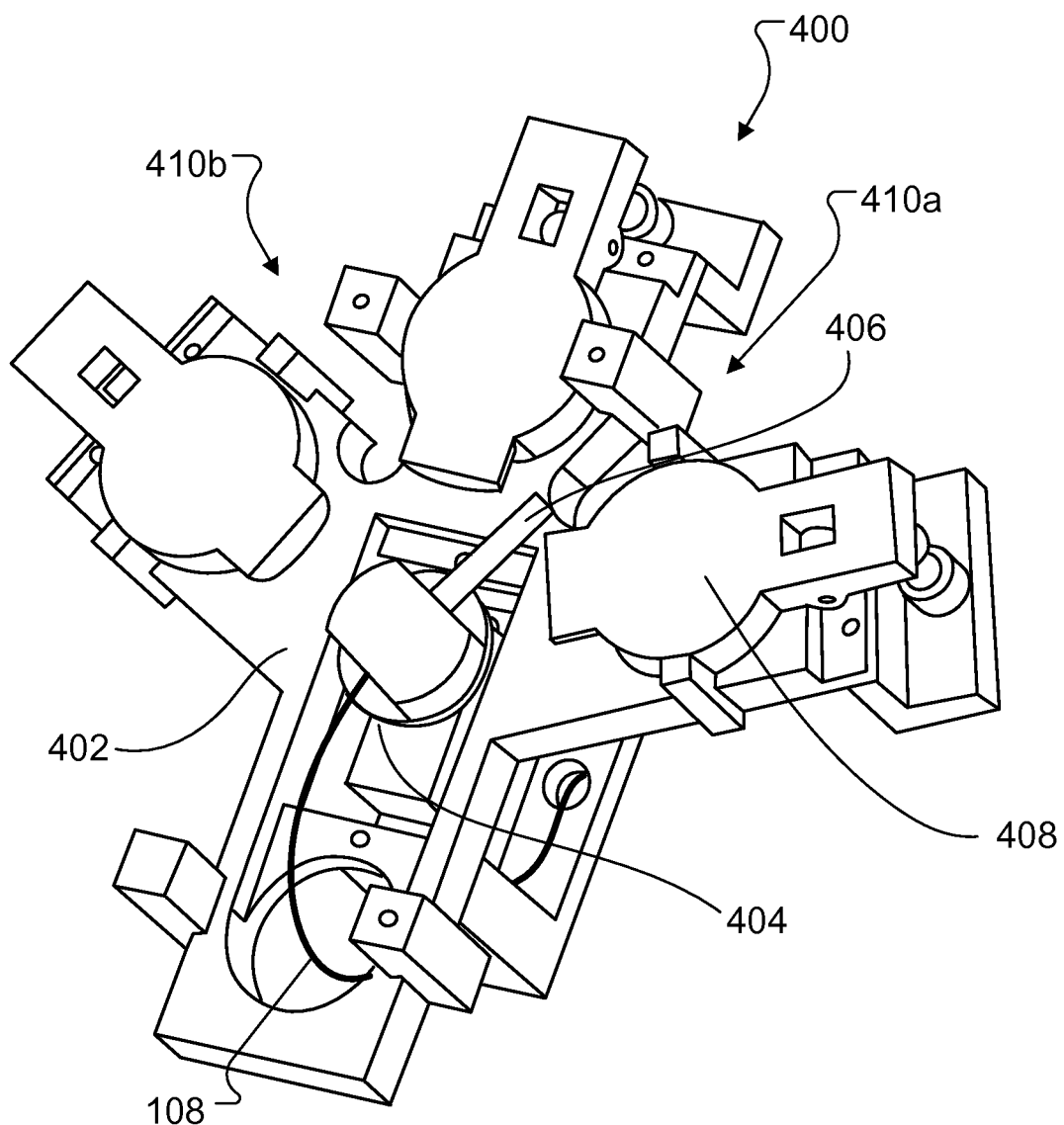
FIG. 4 is a diagram illustrating an example water sampling mechanism that can be used in the water sampling system of the aerial water sampler.

FIG. 4 is a diagram illustrating an example water sampling mechanism 400 that can be used in the water sampling system 106 of the aerial water sampler 100. The water sampling mechanism 400 is held together by a chassis 402. In some examples, the chassis is made of 3D printed acrylonitrile butadiene styrene (ABS) plastic. The chassis 402 can be configured to mate with an airframe of the aerial water sampler 100, e.g., at a number of mount points using any appropriate mounting structures.

The chassis 402 holds three water sample receptacles 408 which can be, e.g., 20 ml screw-top glass vials with spring-hinged lids. The water sampling extension 108 is fluidly coupled to a needle 406, e.g., a rigid plastic tube that directs water into the vials. Water flow is directed to the vials through the needle 406 as controlled by a servo motor 404 under control of the control system 202. The servo motor 404 confines the rotation of the needle 406 in a plane and can rotate, e.g., 160° total, 80° from center in either direction.

The water sample receptacles 408 can be configured so that, for each receptacle, a spring-hinged lid normally holds the receptacle closed. When the servo-rotated needle 406 is moved into position to deposit a water sample, the needle 406 opens the spring-hinged lid. Then, after depositing the water sample, the servo 404 rotates the needle 406 away and the spring-hinged lid closes by action of the spring, securing the water sample within the receptacle.

The servo 404 can be configured to rotate the needle into one of five positions: three water sampling positions and two flushing positions 410a-b used to flush water through the system, cleaning the tubes and the pump of the system. When the needle 406 is directed to the flushing positions 410a-b, water that is pumped through the system is pumped away from the aerial water sampler 100. During a water sampling mission, the needle 406 can be moved in sequence from one side of the mechanism 400 to the other side. By having two flushing positions 410a-b, the risk of cross-contamination can be reduced by avoiding moving the needle 406 past a lid that seals a filled vial.

In some examples, the mechanism 400 includes a break-away mechanism, which allows the water sampling extension 108 and the pump 112 to release from the mechanism 400 if subjected to at least a threshold amount of force, e.g., 15.1 N of force, which can be less than a maximum lifting thrust of the aerial water sampler 100 of 17.7 N. This can prevent the aerial water sampler 100 from getting stuck if the pump 112 or the extension 108 becomes entangled.

Figure 5:
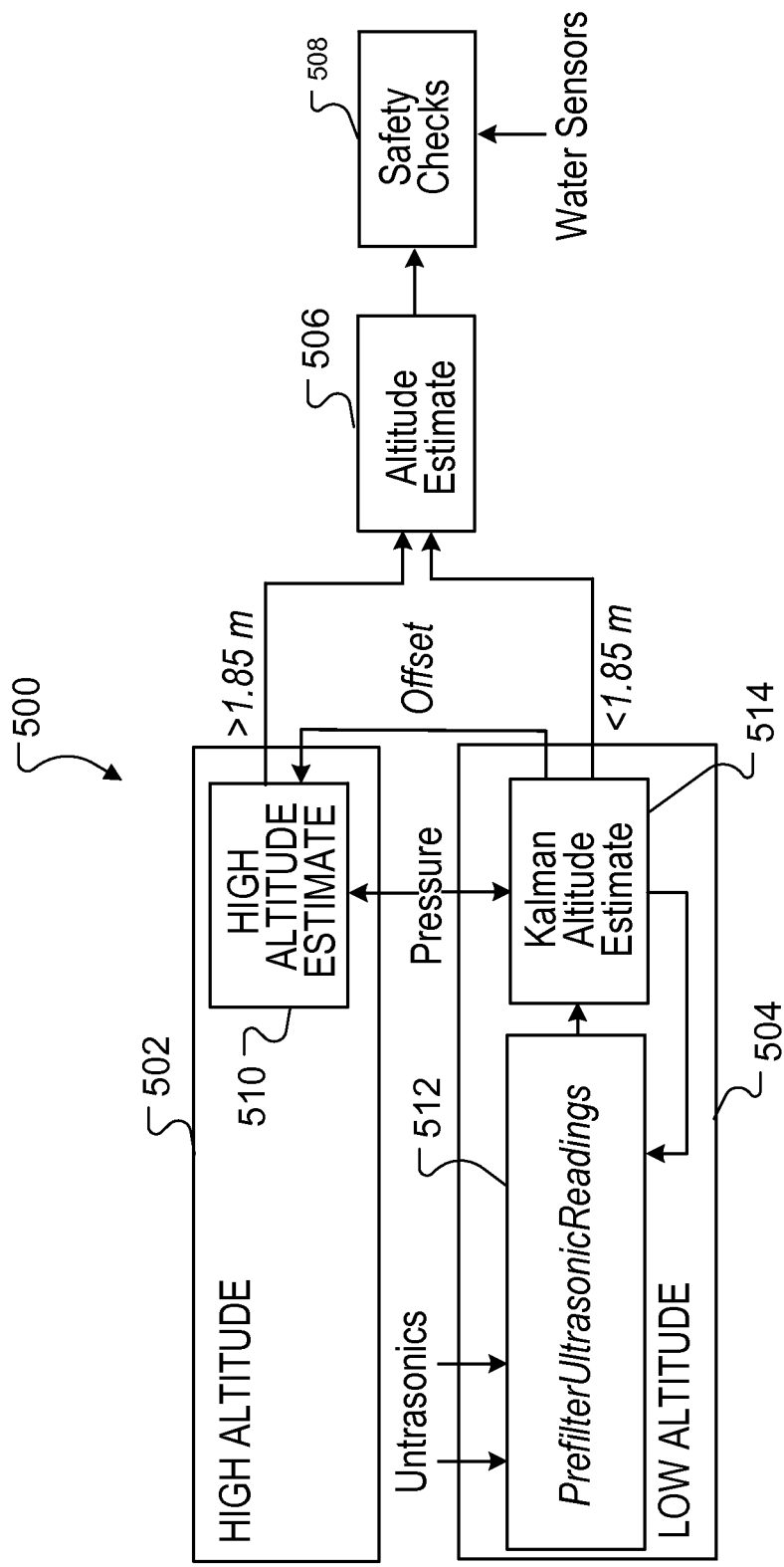
FIG. 5 is a block diagram illustrating an altitude estimation method for the aerial water sampler.
Figure 6A:
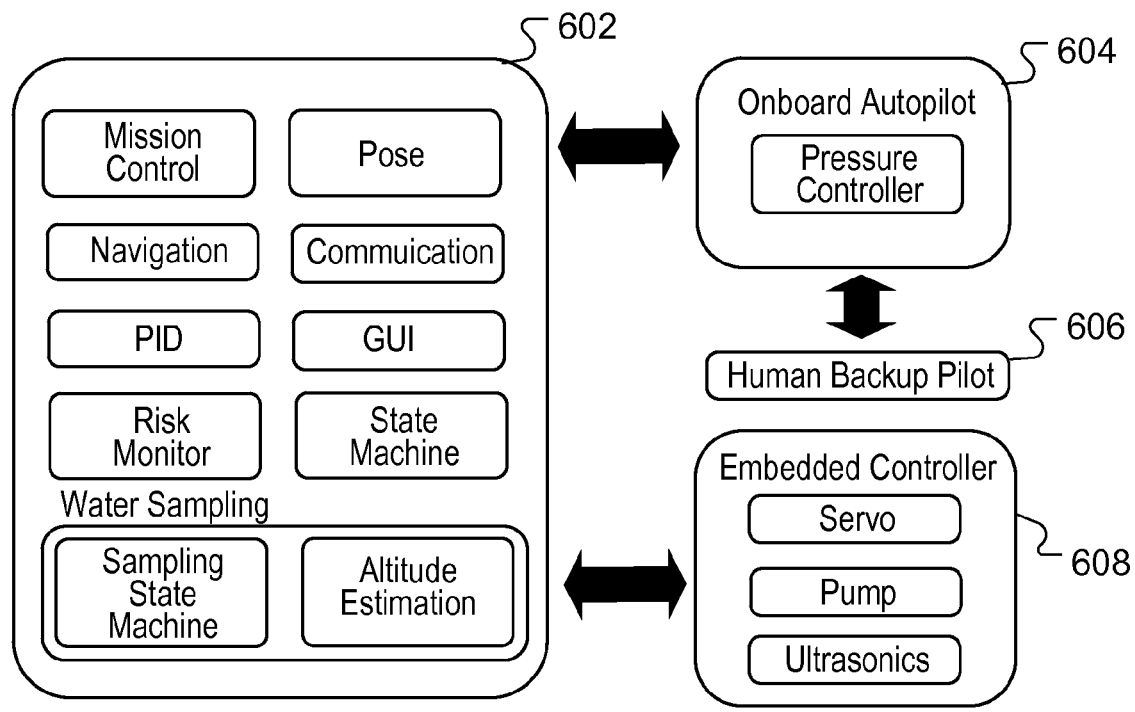
FIGS. 6A-B illustrate an example software architecture for an aerial water sampler.
Figure 6B:
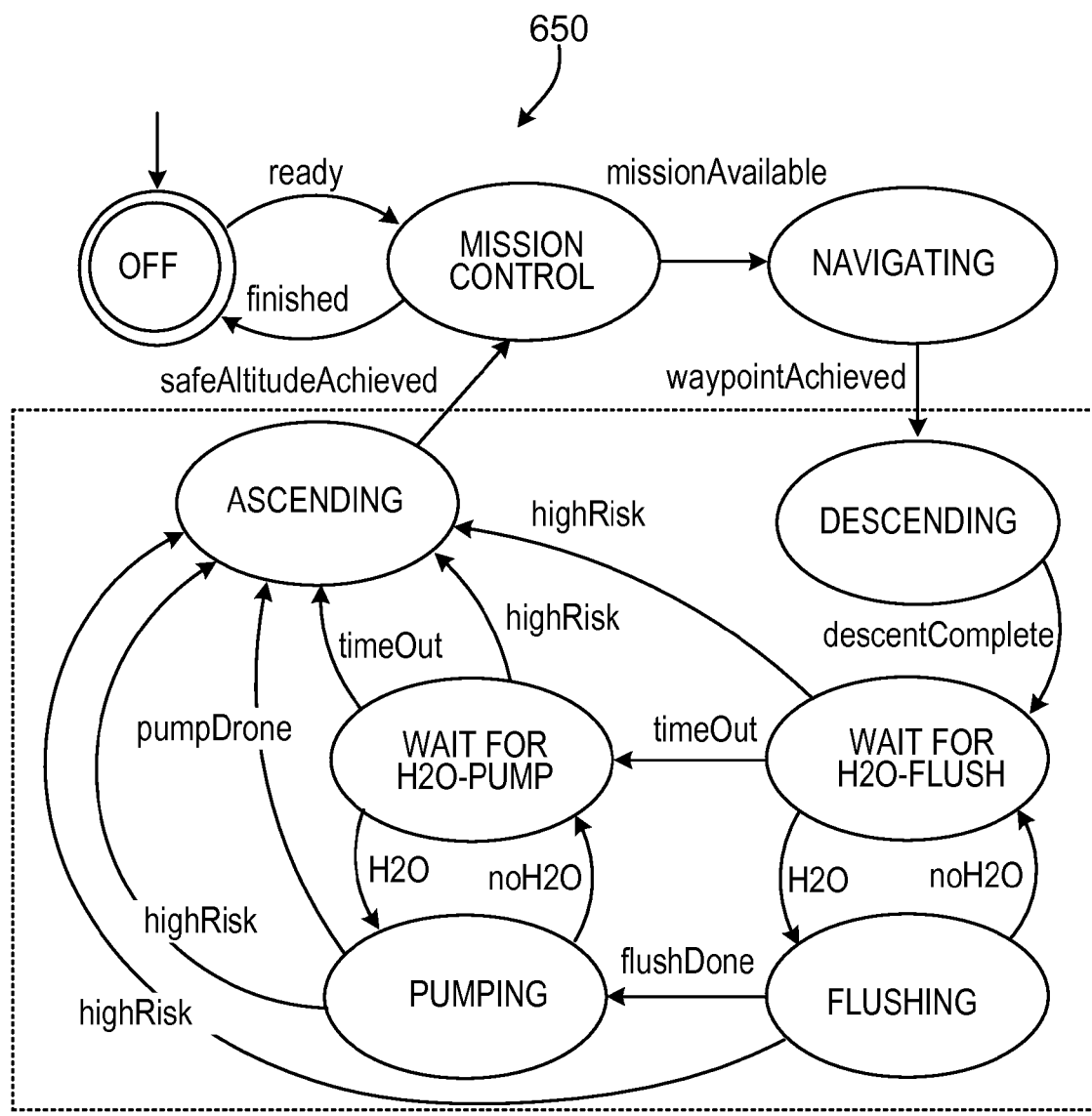

FIG. 5 is a block diagram illustrating an altitude estimation method 500 for the aerial water sampler 100. The method 500 can be performed, e.g., by the control system 202 of the aerial water sampler 100. For purposes of illustration, the method 500 will be described with respect to a system that performs the method.

The system estimates the altitude using a high altitude block 502 when the aerial water sampler 100 is estimated by the system to be at an altitude greater than or equal to a threshold altitude, e.g., 1.85 m, and using a low altitude block 504 when the aerial water sampler 100 is estimated by the system to be at an altitude lower than the threshold altitude.

An altitude estimate block 506 selects between the high altitude and low altitude blocks 502 and 504 depending on the current estimated altitude by the system. The system can perform optional safety checks using a safety check block 508, which can use, e.g., signals from water sensors that a spaced along the water sampling extension 108.

Flying near water can be dangerous to conventional UAVs because the water can damage the electrical and mechanical systems. Some conventional commercial UAVs come equipped with air pressure altimeters and lack sensors to otherwise detect surroundings, especially the surroundings below the UAVs. The air pressure altimeter readers can drift, e.g., by multiple meters, over the time of a flight and can be insufficiently accurate to fly close enough to water to obtain a water sample.

The altitude sensor system 104 of the aerial water sampler 100 includes ultrasonic rangefinders that face the water source 110. The rangefinders can point straight down and can flank the water sampling system 106 by a distance, e.g., 10 cm from the center, to increase the likelihood of an unobstructed path to the water's surface, which might otherwise be blocked by the swinging tube and pump. The rangefinders can emit an ultrasonic pulse that propagates in the shape of a cone. In some examples, the rangefinders are selected to have the smallest cone available, to increase the chance that the rangefinder detects what is below it in the environment and not the tube, which can be below it at a small angle.

Some narrow cone rangefinders stop sensing reliably when not pointing straight down. At large pitch or role angles, e.g., greater than 20° at an altitude of 1.0 m, the rangefinders point away from the vehicle and can report MAX_RANGE. Such angles can be avoided or reduced by approaching the water from above rather than flying close to the water at a steep angle. The system can also be configured to discard large measurements from one or more of the rangefinders. In some examples, each rangefinder is configured to sample at 10 hz, and the sample times can be offset from each other by 50 ms to reduce interference and to increase the rate that altitude information is acquired to 20 hz.

The water conductivity sensors can be spaced apart at intervals along the water sampling extension 108, e.g., at regular intervals of 10 cm from the bottom of the extension up to 50 cm. Using the water conductivity sensors, system can determine to activate the pump after that water conductivity sensors have reported that the pump has been wet for at least a threshold amount of time, e.g. 400 ms.

Referring back to FIG. 5, the low altitude 504 estimation uses a Kalman filter of ultrasonic rangefinder readings and air pressure sensor readings. The high altitude 502 estimation uses readings from the air pressure sensor and an offset from the low altitude estimate. The system can use a scoring heuristic to pre-filter the ultrasonic rangefinder readings, which can be useful due to non-Gaussian noise and incorrect readings resulting from the water sampling extension 108 swinging in front of a rangefinder. Applying the scoring heuristic can include scoring the ultrasonic readings based on the variance or other statistical properties of the readings and possibly discarding ultrasonic readings with statistical properties outside of a predefined or dynamically changing range. The scoring heuristic can be based on an assumption that not all of the rangefinders will be blocked at the same time by the water sampling extension 108 and that the rangefinders will report similar readings when not occluded, due to their physical placement.

An example heuristic is shown as pseudocode in Alg. 1.

Algorithm 1 Prefilter sensor readings to avoid non-gaussian noise and spurious readings. Although our current system uses only two ultrasonics, this prodecure supports multiple sensors.

```
 1: procedure PREFILTERULTRASONICREADINGS(ultrasonicReadings,currentKalmanEstimate)
 2:     max Range = 1.85                                                            ▷ meters
 3:     proximityThreshold = 0.075                                                  ▷ meters, empirical
 4:     varianceThreshold = 0.08                                                    ▷ meters², empirical
 5:     numUltra ← 2
 6:     bestScore ← −1
 7:     sumOfBest Readings ← 0
 8:     countOfBest Readings ← 0
 9:     for i ← 1,i ≤ numUltra,i ← i + 1 do                                         ▷ iterate over all ultrasonics
10:         ultrasonicScore[i] ← 0                                                  ▷ Initialize
11:         if ultrasonicReadings[i] < max Range then                               ▷ ensure range
12:             ultrasonicScore[i] ← 4                                              ▷ highest priority
13:         end if
14:         if abs(currentKalmanEstimate − ultrasonicReadings[i]) < proximityThreshold then ▷ proximity
15:             ultrasonicScore[i] ← ultrasonicScore[i] + 2                         ▷ medium priority
16:         end if
17:         if abs(getVariance(ultrasonicReadings[i],1 sec) < varianceThreshold then ▷ variance
18:             ultrasonicScore[i] ← ultrasonicScore[i] + 1                         ▷ least priority
19:         end if
20:         if ultrasonicScore[i] > bestScore then
21:             bestScore ← ultrasonicScore[i]
22:         end if                                                                  ▷ track best score so far
23:     end for
24:     for i ← 1,i ≤ numUltra,i ← i + 1 do                                         ▷ iterate to find all best scores
25:         if ultrasonicScore[i] = bestScore then
26:             sumOfBest Readings ← sumOfBest Readings + ultrasonicReading[i]
27:             countOfBest Readings ← countOfBest Readings + 1
28:         end if
29:     end for
30:     bestValue ← sumOfBest Readings/countOfBest Readings                         ▷ average
        return min(bestValue,maxRange)                                              ▷ input to Kalman Filter
31: end procedure
```

In addition to keeping the aerial water sampler 100 dry, another reason that having an accurate altitude estimation is useful is that the pump 112 may need to be submerged and primed prior to operation. To confirm that the pump is actually touching water and not just approaching dry ground, and as another potential safety feature, the water sampling extension 108 can be augmented with water conductivity sensors coupled to the control system 202 or the pump 112 or both.

The scoring heuristic can give the strongest preference to readings within the maximum range (less than 1.85 m), and the score can be based on proximity to the current estimate (within 0.075 m). The scoring can be based on a weak preference based on tolerable variance during the last one second (less than 0.08 $m^2$). If more than one rangefinder has the same score, the readings from those rangefinders can be averaged.

At low altitudes, the Kalman estimate can be accurate enough to assure vehicle safety, while at high altitudes, the air pressure sensor is sufficient. When the aerial water sampler 100 ascends from low altitude to high altitude, the pressure sensor readings can be offset using the last estimate from the Kalman filter. When the aerial water sampler 100 descends, the sampler can limit its velocity so that the sampler can stop and hover before coming within one meter of the water.

The water conductivity sensors can be used for additional safety checks. If the water conductivity sensors indicate that the tube is too deep, e.g., if one of the water conductivity sensors higher up the tube signals, then the aerial water sampler 100 can ascend to a safer altitude. In some examples, the readings from the water conductivity sensors are not added to the Kalman filter because those sensors can be slow to respond and because occasional water droplets from the pump can cause false readings.

FIGS. 6A-B illustrate an example software architecture for an aerial water sampler 100. FIG. 6A is a block diagram of software components 600 for both a ground station computing system 602, an onboard autopilot 604, and an embedded controller 608 on the aerial water sampler 100. The ground station 602 can be implemented using the Robot Operating System (ROS) which can handle low-level communication with the aerial water sampler 100, mission control, risk management, navigation, state machines, and altitude estimation.

The embedded controller 608 can receive instructions from the ground station 602, control the water sampling system 106, receive sensor readings from the ultrasonic rangefinders and the water conductivity sensors, and broadcast state information for the subsystems of the aerial water sampler 100. The embedded controller 608 can communicate with the ground station 602 using one or more radio links, e.g., XBee radio links. One or more of the ground station and the embedded controller 608 can implement assessors to detect high risk water sampling or navigating conditions based on sensor readings and to adjust, restart, or abort a mission based on the assessors.

FIG. 6B is a state diagram 650 of a Finite State Automata (FSA) that can be implemented by the example software architecture. Each oval represents a logical state, which can be encoded in the software as a configuration of ground control and embedded system software. The arrows represent state transitions, labelled with descriptions of events that trigger transitions from one state to another. The flow of activities is clockwise starting from the OFF state in the upper-left corner.

From OFF, the system starts when the aerial water sampler 100 and ground station are ready, and then the control flows to MISSION CONTROL. If a mission is available, the system transitions to the NAVIGATING state, where the aerial water sampler takes off and navigates to a specified location. Once the sampler arrives at the specified location (waypointAchieved), the system moves to the DESCENDING state. When the target height has been reached, the system attempts to detect water (WAIT FOR H20—FLUSH), and once water is detected, water is flushed through the tube to clean it.

After flushing completes, the system stats PUMPING, where it captures water in a vial and starts or stops the pump based on whether the water conductivity sensors report H20 or noH2O. After pumping, or if the system takes too long to pump, or if the altitude goes too low (highRisk), then the system transitions to ASCENDING state. This moves the aerial water sampler 100 up away from the water's surface and the possible danger of water damage. After ascending, the system returns to MISSION CONTROL and either starts a new mission or returns to base and ends the program.

The software can be implemented to coordinate the activities using one or more of: 1) waypoints, which the system compares to the determined location of the aerial water sampler, so that the aerial water sampler arrives at the specified sample location and descends to the target height; 2) times, which track how long the pump has actually been pumping and infer that the tube has been sufficiently flushed or that the vial is full, and 3) assessors on sensor values to measure risk and improve the likelihood that the sampling altitude is safe.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims.

What is claimed is:

1. A vehicle comprising:
an aerial propulsion system;
an altitude sensor system comprising a plurality of ultrasonic rangers configured to face the water source;
a water sampling system comprising:
a water sampling extension configured to extend away from the vehicle;
one or more water sample receptacles; and
a water pump; and
a control system configured to perform operations comprising:
guiding, using the aerial propulsion system, the vehicle over a water source;
causing, using sensor data from the altitude sensor system, the vehicle to descend towards the water source so that the water sampling extension contacts the water source, wherein a scoring heuristic is applied to a plurality of ultrasonic readings from the ultrasonic rangers; and
causing, using the water sampling system, the water pump to pump water from the water source into the one or more water sample receptacles through the water sampling extension while the vehicle is in flight over the water source.

2. The vehicle of claim 1, wherein the altitude sensor system comprises:
a plurality of ultrasonic rangers configured to face the water source; and
an air pressure sensor.

3. The vehicle of claim 2, wherein guiding the vehicle comprises determining that the altitude of the vehicle is greater than a threshold altitude and, in response, using the air pressure sensor to estimate the altitude of the vehicle and guide the vehicle.

4. The vehicle of claim 2, wherein causing the vehicle to descend towards the water source comprises estimating the altitude of the vehicle using a Kalman filter and a plurality of ultrasonic readings from the ultrasonic rangers and a plurality of pressure readings from the air pressure sensor.

5. The vehicle of claim 1, wherein applying the scoring heuristic comprises discarding ultrasonic readings outside of a programmed maximum range of the ultrasonic sensors.

6. The vehicle of claim 1, wherein applying the scoring heuristic comprises scoring the ultrasonic readings based on a respective proximity, for each ultrasonic reading, to a current altitude estimate maintained by the control system.

7. The vehicle of claim 1, wherein the vehicle is an unmanned rotorcraft including a plurality of rotors.

8. The vehicle of claim 7, wherein the control system is configured to autonomously guide the vehicle to a plurality of water sampling sites and cause the water sampling system to store a water sample from each of the water sampling sites into a respective water sample receptacle.

9. The vehicle of claim 8, wherein the operations comprise, after guiding the vehicle to a second water sampling site, flushing water from the water sampling system from a first water sampling site using water from the second water sampling site.

10. A method performed by a vehicle, the method comprising:
guiding, using an aerial propulsion system, the vehicle over a water source;

causing, using sensor data from an altitude sensor system comprising a plurality of ultrasonic rangers configured to face the water source, the vehicle to descend towards the water source so that a water sampling extension of the vehicle contracts the water source, wherein a scoring heuristic is applied to a plurality of ultrasonic readings from the ultrasonic rangers; and causing, using a water sampling system comprising a water pump, the water pump to pump water from the water source into one or more water sample receptacles through the water sampling extension while the vehicle is in flight over the water source.

11. The method of claim 10, wherein the altitude sensor system comprises:
  a plurality of ultrasonic rangers configured to face the water source; and
  an air pressure sensor.

12. The method of claim 11, wherein guiding the vehicle comprises determining that the altitude of the vehicle is greater than a threshold altitude and, in response, using the air pressure sensor to estimate the altitude of the vehicle and guide the vehicle.

13. The method of claim 11, wherein causing the vehicle to descend towards the water source comprises estimating the altitude of the vehicle using a Kalman filter and a plurality of ultrasonic readings from the ultrasonic rangers and a plurality of pressure readings from the pressure sensor.

14. The method of claim 10, wherein applying the scoring heuristic comprises discarding ultrasonic readings outside of a programmed maximum range of the ultrasonic sensors.

15. The method of claim 10, wherein applying the scoring heuristic comprises scoring the ultrasonic readings based on a respective proximity, for each ultrasonic reading, to a current altitude estimate maintained by the control system.

16. The method of claim 10, wherein the vehicle is an unmanned rotorcraft including a plurality of rotors.

17. The method of claim 16, comprising autonomously guiding the vehicle to a plurality of water sampling sites and causing the water sampling system to store a water sample from each of the water sampling sites into a respective water sample receptacle.

18. The method of claim 17, comprising, after guiding the vehicle to a second water sampling site, flushing water from the water sampling system from a first water sampling site using water from the second water sampling site.

19. A an unmanned rotorcraft comprising:
  a plurality of rotors;
  an aerial propulsion system;
  an altitude sensor;
  a water sampling system comprising:
    a water sampling extension configured to extend away from the vehicle;
    one or more water sample receptacles; and
    a water pump; and
  a control system configured to autonomously guide the unmanned rotorcraft to a plurality of water sampling sites by performing, for each of the plurality of water sampling sites, operations comprising:
    guiding, using the aerial propulsion system, the vehicle over a water source;
    causing, using sensor data from the altitude sensor system, the vehicle to descend towards the water source so that the water sampling extension contacts the water source;
    causing, using the water sampling system, the water pump to pump water from the water source into the one or more water sample receptacles through the water sampling extension while the vehicle is in flight over the water source; and
    causing the water sampling system to store a water sample from the water source in a respective water sample receptacle.

20. The rotorcraft of claim 19, wherein the operations comprise, after guiding the vehicle to a second water sampling site, flushing water from the water sampling system from a first water sampling site using water from the second water sampling site.

* * * * *